United States Patent
Steindl (10) Patent No.: US 6,706,486 B1
(45) Date of Patent: Mar. 16, 2004

(54) METHOD FOR THE QUANTITATIVE RELEASE OF NATURAL OR RECOMBINANT PROTEINS, POLYPEPTIDES OR PEPTIDES

(75) Inventor: Franz Steindl, Vienna (AT)

(73) Assignee: Amersham Biosciences AB, Uppsala (SE)

( * ) Notice: Subject to any disclaimer, the term of this patent is extended or adjusted under 35 U.S.C. 154(b) by 0 days.

(21) Appl. No.: 09/719,512

(22) PCT Filed: May 14, 1999

(86) PCT No.: PCT/SE99/00828

§ 371 (c)(1),
(2), (4) Date: Feb. 15, 2001

(87) PCT Pub. No.: WO99/66325

PCT Pub. Date: Dec. 23, 1999

(30) Foreign Application Priority Data

Jun. 19, 1998 (AT) .............................................. 1068/98

(51) Int. Cl.$^7$ ........................ G01N 33/53; G01N 33/543
(52) U.S. Cl. ........................ 435/7.1; 435/7.92; 435/174; 435/7.94; 435/814; 435/961; 436/147; 436/174; 436/175; 436/501; 436/512; 436/518; 436/524; 436/825; 436/826; 422/68.1; 424/184.1; 424/193.1
(58) Field of Search .............................. 435/7.1, 7.92, 435/7.94, 174, 814, 961; 436/501, 518, 524, 512, 147, 174, 175, 825, 826; 424/184.1, 193.1; 422/68.1

(56) References Cited

U.S. PATENT DOCUMENTS

| | | | |
|---|---|---|---|
| 4,092,114 A | 5/1978 | Buck | 23/230 |
| 4,752,571 A | 6/1988 | Berglund et al. | 435/7 |
| 5,556,745 A | 9/1996 | Schupbach et al. | 435/5 |

FOREIGN PATENT DOCUMENTS

| | | |
|---|---|---|
| AT | 403 378 B | 1/1998 |
| EP | 0 213 093 | 3/1987 |
| EP | 0 338 591 | 10/1989 |
| EP | 0 657 530 A2 | 6/1995 |

OTHER PUBLICATIONS

A. Forsgren, et al. "'Protein A' from S. Aureus" The Journal of Immunology, vol. 97, No. 6, 1966, pp. 822–827.
G. Kronvall "A Surface Component in Group A, C, and G Streptococci with Non–Immune Reactivity for Immunoglobulin G" The Journal of Immunology, vol. 3, No. 5, Nov. 1973 pp. 1401–1406.
M. Inganas, et al. "Further Characterization of the Alternative Protein–A Interaction of Immunoglobulins: Demonstration of an Fc–Binding Fragment of Protein A Expressing the Alternative Reactivity" Scand. J. Immunol., vol. 14, 1981 pp. 379–388.
M. Erntell, et al. "Alternative Non–Immune F(ab<)2–Mediated Immunoglobulin Binding to Group C and G Streptococci" Scand. J. Immunol., vol. 17, 1983 pp. 201–209.
K. Potter, et al. "Staphylococcal Protein A Simulatneously Interacts with Framework Region 1, Complementarity–Determining Region 2, and Framework Region 3 on Human Vh3–Encoded lgs1" The Journal of Immunology, vol. 157, No. 7, 1996 pp. 2982–2988.
K. Potter, et al. "Staphylococcal Protein A Binding to Vh3 Encoded Immunoglobulins" Intern. Rev. Immunol., vol. 14, 1997 pp. 291–308.
M. Eliasson, et al., "Differential IgG–Binding Characteristics of Staphylococcal Protein A, Streptococcal Protein G, and A Chimeric Protein AG " The Journal of Immunology, vol. 14, No. 2, Jan. 15, 1989 pp. 575–581.
T. Moks, et al. "Staphylococcal Protein A Consists of Five IgG–Binding Domains" Eur. J. Biochem., vol. 156, 1986 pp. 637–643.
M. Inganas, et al. "Interaction of Human Polyclonal IgE and IgG from Different Species with Protein A from Staphylococcus Aureus: Demonstration of Protein–A–Reactive Sites Located in the Fab2 Fragment of Human IgG" Scand. J. Immunol., vol. 12, 1980 pp. 23–31.
M. Inganas "Comparison of Mechanisms of Interaction Between Protein A from Staphylococcus Aureus and Human Monoclonal IgG, IgA and IgM in Relation to the Classical Fcy and the Alternative F(ab')2e and Protein A Interactions" Scand. J. Immunol., vol. 13, 1981 pp. 343–352.
P. Roben, et al. "Vh3 Family Antibodies Bind Domain D of Staphylococcal Protein A" The Journal of Immunology, vol. 154, 1995 pp. 6437–6445.
P. Akesson, et al. "Protein H—A Novel IgG Binding Bacterial Protein" Molecular Immunology, vol. 27, No. 6, 1990 pp. 523–531.
M. Wilson, et al. "Clusterin Binds by a Multivalent Mechanism to the Fc and Fab Regions of IgG" Biochimica et Biophysica Acta, 1159, 1992 pp. 319–326.

(List continued on next page.)

Primary Examiner—Long V. Le
Assistant Examiner—Kartic Padmanabhan
(74) Attorney, Agent, or Firm—Stephen G. Ryan; Royal N. Ronning, Jr.; Yonggang Ji (57) ABSTRACT

The present invention relates to a method for the quantitative release of natural or recombinant proteins, polypeptides (thermostable immunoligands) able to bind to the Fc-part of immunoglobulins (antibodies, in particular of the IgG class and primarily becoming bound outside the paratope) from complexes in various sample matrixes in order to make these released natural or recombinant proteins, polypeptides or peptides quantitatively available in immunochemical assays and to keep them quantitatively available. The method is characterized by mixing the sample with reagent compound that is able to bind non-specifically to immunoglobulins, and thereafter subjecting the sample to a heat treatment step followed by a cooling step.

25 Claims, 8 Drawing Sheets

OTHER PUBLICATIONS

W. Bensinger, et al. "Clinical Trials with Staphylococcal Protein A" Journal of Biological Response Modifiers, vol. 3, 1984 pp. 347–351.

G. Messerschmidt, et al. "Clinical Trials with Staphylococcus Aureus and Protein A in the Treatment of Malignant Disease" Journal of Biological Response Modifiers, vol. 3, 1984 pp. 325–329.

D. Terman, et al. "Antitumor Effects of Immobilized Protein A and Staphylococcal Products: Linkage Between Toxicity and Efficacy, and Identification of Potential Tumoricidal Reagents" Eur. J. Cancer Clin. Oncol., vol. 21, No. 10, 1985 pp. 1115–1122.

G. Ventura, et al. "Clinical Trial of Plasma Perfusion Over Immobilized Staphylococcal Protein A in Metastatic Breast Cancer" Cancer Treatment Reports, vol. 71, No. 4, Apr. 1987 pp. 411–413.

J. Langone "Protein A of Staphylococcus Aureus and Related Immunoglobulin Receptors Produced by Streptococci and Pneumonococci" Advances in Immunology, vol. 32, 1982 pp. 157–252.

J. Langone, et al. "Radioimmunoassays for Protein A of Staphylococcus Aureus" Journal of Immunological Methods, No. 63, 1983 pp. 145–157.

S. Knicker, et al. "Immunoassay to Measure Staphylococcal Protein A in the Prescence of Murine Immunoglobulins" Journal of Immunological Methods, No. 142, 1991 pp. 53–59.

J. Schupbach, et al. "Heat–Mediated Immune Complex Dissociation and Enzyme–Linked Immunosorbent Assay Signal Amplificaton Render p24 Antigen Detection in Plasma as Sensitive as HIV–1 RNA Detection by Polymerase Chain Reaction" AIDS 1996, vol. 10, No. 10 pp. 1085–1090.

J. Clark, Jr., et al. "Experimental Biochemistry—Second Edition" 1964 and 1977 by W.H. Freeman and Company p. 49.

Fig. 5: Schematic representation of the test design and test procedure

METHOD FOR THE QUANTITATIVE RELEASE OF NATURAL OR RECOMBINANT PROTEINS, POLYPEPTIDES OR PEPTIDES

This is the U.S. National Stage filing of PCT/SE99/00828 filed on May 14, 1999.

BACKGROUND OF THE INVENTION

1. Field of the Invention

The present invention relates to a method for the quantitative release of natural or recombinant proteins, polypeptides or peptides (thermostable immunoligands) able to bind to the Fc-part of immunoglobulins (antibodies, in particular of the IgG class and primarily becoming bound outside the paratope) from complexes in various sample matrixes in order to make these released natural or recombinant proteins, polypeptides or peptides quantitatively available in immunochemical assays and to keep them quantitatively available. The method of release is primarily intended to be used as a prestep in the immunoassay of the kind of proteins, polypeptides and peptides just mentioned when they exist as contaminants in various immunoglobulin/antibody preparations or as more or less pure preparations.

In the context of the present application, the term "of bacterial origin" refers to a polypeptide or protein which is, derived from polypeptide or protein that is produced naturally by bacteria or other microorganisms. "Recombinant" designates a protein, a polypeptide or a shorter antibody binding fragment expressed in any type of cells by means of genetic engineering. "Synthetic peptide" means that the part of a protein or polypeptide which contains the functional region is produced by means of chemical peptide synthesis.

2. Description of Related Art

Naturally occurring proteins that are able to bind to the Fc part of primarily class G immunoglobulins (Ig) (IgG) of most mammals are mainly of bacterial origin. The binding strength differs according to species and subclass. This property was first described regarding protein A (SPA) of staphylococcus aureus in 1966 (Forsgren A., Sjöquist J. J. Immunol. 1966;17:822–27) and, a little later, regarding protein G (SPG) of streptococcus pneumoniae in 1973 (Kronvall G., J. Immunol. 1973;111:1401–06). These proteins bind to antibodies in the region between the constant domains 2 and 3 (CH2 and CH3) of the heavy chains. Proteins A and G are known to be able to bind additionally to the variable region of the heavy chains of IgA, IgE, IgG and IgM, which Igs belong to the VH3 family (Inganäs M. et al., Scand. J. Immunol. 1981; 14:379–88 and Erntell M. et al., Scand. J. Immunol. 1983; 17:201–09). Amino acids of three sections in the variable region of the heavy chains of the antibodies (FR1, CDR2 and FR3) are involved in this so-called "alternative reactivity" (Potter K N. et al., J. Immunol. 1996;157(7):2982–88 and Potter K N. et al., Int. Rev. Immunol. 1997;14(4):291–308). Proteins A and G bind antibodies either at the same site or, at least, at closely overlapping sites (Eliasson M. et al., J. Immunol. 1989;142 (2):575–81). Protein A has 5 (A–E) IgG binding subunits (Moks T. et al., Eur.J.Biochem. 1986; 153(3):637–43). The "alternative reactivity" may be a function of all-single domains, however, it has successfully been examined for two fragments (domains), for domain B (Inganäs M. et al., Scand.J.Immunol. 1980;12:23–31, Inganäs M. et al., Scand.J.Immunol. 1981;13:343–352, Inganäs M. et al., Scand.J.Immunol. 1981;14:379–388) and for domain D (Roben P W. et al., J. Immunol. 1995;154(12):6437–45).

Apart from proteins A and G, further antibody binding proteins are known, which, however, have different specificities and binding regions, such as, e.g., protein H (Akesson P. et al., Mol. Immunol. 1990;27(6):523–31) or clusterine (Wilson M R. et al., Biochim. Biophys. Acta 1992; 1159(3):319–326). The above mentioned IgG binding proteins, polypeptides and peptides (binding outside the paratope) are relatively resistant to heat treatment (in solution) and will therefore in the present document be referred to as thermostable immunoligands.

These proteins (particularly protein A) are used in a variety of applications and are employed on a large scale mainly in the purification of monoclonal and polyclonal antibodies. Both the native and recombinasnt forms are used as ligands in immunoaffinity chromatography. This refined technology provides highly effective purification of antibodies from complex solutions. The antibodies are usually bound at moderate pH to a chromatographic matrix carrying as ligand one of these immunoglobulin-binding proteins and desorbed in an acid environment (pH=2.7–3.5, or 2.7–3.2). Under these conditions, however, it has been impossible so far to avoid a certain degree of ligand leakage.

This is of major importance for antibody preparations used for clinical applications. Protein A (the same applies to protein G) is assumed to have high biological activity, and many publications describe toxic effects in animal models and in humans (Bensinger W I. et al., J. Biol. Response Mod. 1984; 3 (3):347–51, Messerschmidt G L. et al., J. Biol. Response Mod. 1984;3(3):325–29, Terman D S. et al., Eur. J. Cancer Clin. Oncol. October 1985; 21(10):1115–22, Ventura G J. et al., Cancer Treat. Rep. April 1987; 71(4):411–13). Along with enterotoxines A and B, protein A is also thought to play a role in the pathogenicity of staphylococcus aureus infections. Due to its "alternative reactivity", it can also cause mitogenic stimulation of family VH3 B-cells. Therefore, it is essential that these ligands can be identified sensitively, specifically and, above all, correctly, in immunoglobulin preparations.

Many publications and review articles deal with possible ways to use polypeptides able to bind to the Fc-part of antibodies, and with their potential dangers when present as contaminants in products for clinical applications (e.g. Langone J J. et al., J. Adv. Immunol. 1982;17:157–252).

So far, immunochemical assays, such as ELISA (Enzyme Linked Immuno Sorbent Assay) or RIA (Radio Immuno Assay) have been employed in different variations to detect and quantify Ig-binding proteins and/or polypeptides.

One problem with this type of assays is that an Fc(IgG)-binding protein (analyte) will form complexes with the Fc part of antibodies/immunoglobulin G with different affinity depending on the species, IgG subclass and even antibody. This has previously been solved by using either antibody fragments (Fab, Fab$_2$') or specific chicken antibodies (which are not bound by proteins A or G at the Fc-part) for detection (e.g. Langone J J. et al., J. Immunol. Meth. 1982;63:145–57).

In order to release Fc(IgG)-binding proteins and polypeptides from the Fc part of IgG in order to identify them in the presence of IgG, the samples have conventionally been assayed in an acid environment (pH=3.2 or 3.5, respectively) (Berglund A. and Inganäs M., U.S. Pat. No. 4,752,571, 1988; Knicker S. et al., J. Immunol. Meth. 1991; 142:53–59). This method is useful, for instance, to determine protein A in samples containing mouse IgG (various subclasses) at a concentration of up to 250 µg of IgG/ml.

This previously known method has the following limitations:

1. Not all antibody-ligand complexes can be broken up under the conditions used previously. The efficiency of this method depends on the species, the amount of antibodies and the sample matrix. This method is particularly unsuitable for human IgG and plasma and serum samples.

2. It is not possible to further reduce the pH, as would be necessary in many cases, because this would also prevent the reaction with the antibodies used in the assay.

3. Acidification of the samples leads to protein precipitation of various intensity depending on the sample matrix, which causes variable degrees of loss of the proteins or peptides to be detected.

4. Slight deviations in pH lead to different reaction behaviour in the assay and may cause the standard protein dilutions and sample dilutions to react with different intensity in the assay.

It has been suggested to use a combination of SDS (sodium dodecyl hydrogensulfate) and DETAPAC (diethylene triamine-pentaacetic acid) combined with a heating step in order-to make immune complexed antigen molecules (bound by the Fab parts of antibodies) available for immunoassays (AT 403,378 A1, Steindl F.). The release of the antigen depends on the fact that the treatment renders complexing via the antigen binding part (Fab) of the antibody difficult. However, binding at the Fc-Part of IgG is something else than Fab-binding.

Accordingly, for the detection in general of proteins or polypeptides (thermostable immunoligands) recognizing only regions in individual chains of antibodies, however, this method is unsuitable for the following reasons:

1. The renaturation of the heavy chains,in the Fc region and thus the re-binding of such proteins and polypeptides to the heavy chains is not prevented in an optimal way.

2. Various molecules used as buffer ions in affinity chromatography, particularly those containing amino groups (amino acids, e.g. glycine, histidine, or molecules, such as TRIS) also adsorb SDS during heat treatment and thus reduce efficiency. These effects make it hard to adapt the SDS concentration to the protein concentration, particularly in samples having a low protein content.

3. The reagent solution used has only very little buffer capacity (regarding pH). As this method has been optimized primarily for plasma and serum samples, optimum adjustment of the SDS concentration requires previous knowledge of the samples (protein content, type of buffer ions in the sample). This means that the method is not generally applicable. In the case of aunknown samples, it is usually impossible to find the optimum SDS concentration at the first attempt.

4. The period of heat treatment is too short and the SDS concentration is not high enough to optimally denaturate the tertiary structure of antibodies and thus of the specific antigen binding regions (paratopes) and to maintain quantitative dissociation in the sample dilutions for the assay.

BRIEF SUMMARY OF THE INVENTION

In view of the needs of the prior art, the present invention provides a method for releasing thermostable immunoligands that are bound to the Fe-part of immunoglobulins in immunoglobulin-immunoligand complexes. The method includes the step of mixing a sample containing said immunoglobulin-immunoligand complexes with a reagent compound that binds non-specifically or adsorbs to said immunoglobulins and heating said sample mixed with reagent compound and thereafter cooling said sample mixed with reagent compound.

DETAILED DESCRIPTION OF THE PREFERRED EMBODIMENTS

EXAMPLES

It is an object of the present invention to overcome the disadvantages of the prior art methods for dissociating complexes between Fc-binding proteins and the Fc part of antibodies/IgG.

According to the present invention, this object is achieved by mixing the sample with a reagent compound that is able to bind non-specifically to immunoglobulins, and thereafter subjecting the sample to a heat treatment step followed by a cooling step. After the cooling step the sample may be subjected to further treatments, for instance assaying for the presence and/or amount of a thermostable immunoligand that is able to bind to immunoglobulins outside the paratope. In further embodiments of the invention a buffer and/or protein are added before the heating step in order to compensate for sample variations in pH and in protein content, respectively. Furthermore, a chelator may be added before the heating step in order to bind heavy metal ions that may be present.

The reagent compound that is able to bind non-specifically to immunoglobulins may be any compound that has this property and that may remain bound during the heating step. Examples are compounds that may be used in polyacryl amide gel electrophoresis for separating proteins according to molecular weight, for instance SDS-PAGE, and that are active by encapsulating protein molecules in order to give them an overall charge. One of the characteristic features of this type of reagent compounds is that they have hydrophobic as well as negatively charged ends. They will further on be referred to as SDS-like compounds based on the fact that the most preferred compound is sodium dodecyl sulfate (SDS). The concentration range for the SDS-like compounds in the sample before the heating step may be within the range of 10 to 40 mM, preferably 30 to 40 mM.

The heating step is normally applied during a time period within the range of 3 to 180 minutes and at a temperature within the range of 60 to 100° C., the important matter being that the conformation in the Fc part is changed so that the thermostable ligand no longer binds to any significant degree to immunoglobulin after cooling the sample.

Cooling means that the temperature after the heating step is allowed to go down to the temperature that is to be applied for the subsequent-step. This means within the range of 0° to 40° C., for instance 4° to 35° C., which in particular applies to immunoassays.

The pH during the heating step is normally within the range of 5 to 8, the preferred range being 6 to 7,5. The buffering components are preferably selected so as to provide sufficient buffering capacity within these ranges. This also means that the preferred acid-base systems have pKa values within the same pH ranges or close thereto.

Many of the samples contemplated, in particular those obtained in affinity chromatography utilizing thermostable ligands often contain buffering components which are derived from amines and/or amino acids and therefore may appear as positive ions. This type of components easily neutralize negatively charged SDS-like molecules. This means that among buffer substances those that are negatively charged are preferred.

Generally, this means that phosphate or borate buffers are preferred to be added to the sample before the heating step.

The concentration of the buffer in the sample before the heating step should be selected within the range of 5 to 100 mM, such as 20 mM, which particularly applies for borate and phosphate buffers.

The chelating compound may be any chelator that efficiently chelates the various heavy metal ions that may be present in the samples contemplated or as contaminants in any of the added reagents. Examples are EDTA (ethylene diamine tetraacetic acid) and DETAPAC (diethylene triamine pentaacetic acid). The added chelator should be present in the sample before the heating step within the concentration range of 0.5 to 5 mM.

Proteins may be added before the heating step so that the protein concentration will be in the range of 1/20 to 1/100 of the concentration of added SDS, i.e. 0.1 to 2 mM, preferably 0,3 to 2 mM. Suitable proteins may be any proteins that do not interfere with the releasing step or with any subsequent step, for instance the immunoassay steps. The proteins to be used are best represented by albumin of various origins.

Possible samples are, for instance, antibody and other immunoglobulin eluates obtained from affinity adsorbents containing any of the above mentioned thermostable immunoligands as affinity ligands, further processed solutions in various buffers and with and without additives, final formulations for clinical purposes; and native plasma or serum samples and any other samples that may be contaminated with the above mentioned thermostable immunoligands. The samples may also be various preparations of purified forms of the thermostable immunoligands.

According to a preferred embodiment of the present invention, the samples are brought into a uniform sample matrix by means of predilution with a preferably phosphate buffered solution having a defined protein content, and mixed with a defined reagent adjusted to this sample matrix in order to release thermostable immunoligands. This defined reagent comprises sodium dodecyl sulfate (SDS) and a chelating agent, such as DTPA or EDTA. The samples are mixed with the reagent, heated, and subsequently cooled to room temperature. Possible samples are, for instance, all antibody eluates in immunoaffinity chromatography, processed antibody solutions in various buffer solutions with and without additives, final formulations for clinical purposes, and native plasma and serum samples.

In the case of unknown (not defined) samples, the sample is preferably mixed with the phosphate buffered protein solution at a ration of 1:4, and this mixture is then mixed with the reagent solution at a ration of 1:2. Thus, the method can be easily adapted to the consumption by the present protein matrix, preventing disturbing influences caused by the reaction solution components in subsequent assays, e.g. ELISAs.

In the case of defined samples containing no buffer systems containing amino groups, the dilution ratio can be reduced, maintaining an appropriate protein:SDS ratio.

In order to prevent renaturation of the heavy chains of IgG antibodies and thus to keep ligands and heavy chains from re-binding before or during detection, the reagent is added proportionately to the sample dilution buffer used in the assay for quantitative analysis. This keeps the SDS molecules adsorbed to the heavy chains from being desorbed by the dilution of the samples to such an extent that the reduction in the number of negative charges would allow renaturation (refolding) of the binding sites. Renaturation is effectively prevented at a free SDS concentration of 0.02% without adversely affecting the assay.

For instance, the method according to the present invention is carried out as follows.

Samples containing ligands entirely or partly in bound form as antibody-ligand-complexes are mixed with a phosphate buffered defined protein solution at a ratio of 1:4 and subsequently mixed with the reagent solution in sealable reaction vessels at a ratio of 1:2. Subsequently, the reaction vessels are subjected to heat treatment (2 h at 100° C.) and then cooled to room temperature.

The present invention allows constant release of the ligands from the antibody-ligand-complexes. Thanks to the, e.g., phosphate buffered defined protein solution, the method of the present invention offers sufficient buffer capacity for differences in pH, protein content and composition of the samples in order to allow uniform use of the reagent solution. The pH of the two reaction solutions, i.e. the defined protein solution and the reagent solution, is particularly desirably adjusted to 6.0–7.5, such as 6.0–7.0, e.g. by means of 1N NaOH or 1N HCl. Furthermore, heat treatment is preferably carried out at 100° C. for up to 120 min. The stated mixing ratio will also buffer a varying amount of remaining free SDS molecules in order to prevent negative effects caused by excessively high concentrations in the subsequent quantitative immunochemical assay (e.g. ELISA).

Moreover, the addition of reagent solution to the sample dilution buffer in the assay will correspondingly work against renaturation of the heavy chains of antibodies, preventing desorption of SDS molecules and thus re-binding of the ligands.

At a preferred mixing ratio of 1 (sample):4 (protein solution):10 (reagent solution), the protein solution and the reagent solution are used at the following optimum concentrations:

Phosphate buffered solution having defined protein content:
1.15 g/l of $Na_2HPO_4.2\ H_2O$
0.2 g/l of $KH_2PO_4$
0.2 g/l of KCl
8 g of NaCl
50 g/l of bovine serum albumin or egg albumin or another albumin per litre.
pH=6–7.5, such as 6–7 (adjust with 1N HCl)

Reagent solution:
 SDS 15 g/l
 DTPA 1 g/l

Possible denaturations of ligands are compensated for by prediluting and treating the standard in the defined protein solution and reagent solution in exactly the same way.

The method according to the present invention aims at eliminating negative and, in addition, very variable influences by different sample components, which prevent quantitative analysis in the assay. E.g. in ELISA, this aim is reached if the measured extinctions of the dilution series of the standard protein and of the samples containing antibodies are similar in slope. This problem has remained unsolved in protein A detection for antibodies reacting most intensively with protein A (e.g. human and canine IgG), or, generally, in the case of very high antibody concentrations (>1 mg/ml). Furthermore, ever so often it has not been possible to quantify protein A correctly if specific (anti-protein A) antibodies are present in the sample.

FIG. 1a–1d: A comparison of retrieval native staphylococcus aureus-protein A (SPA) by means of ELISA added to human plasma in relation to the incubation period at 100° C. (in a water bath, 0, 30, 60, and 120 min). These samples were diluted according to the method of the present invention.

Figure 1A:
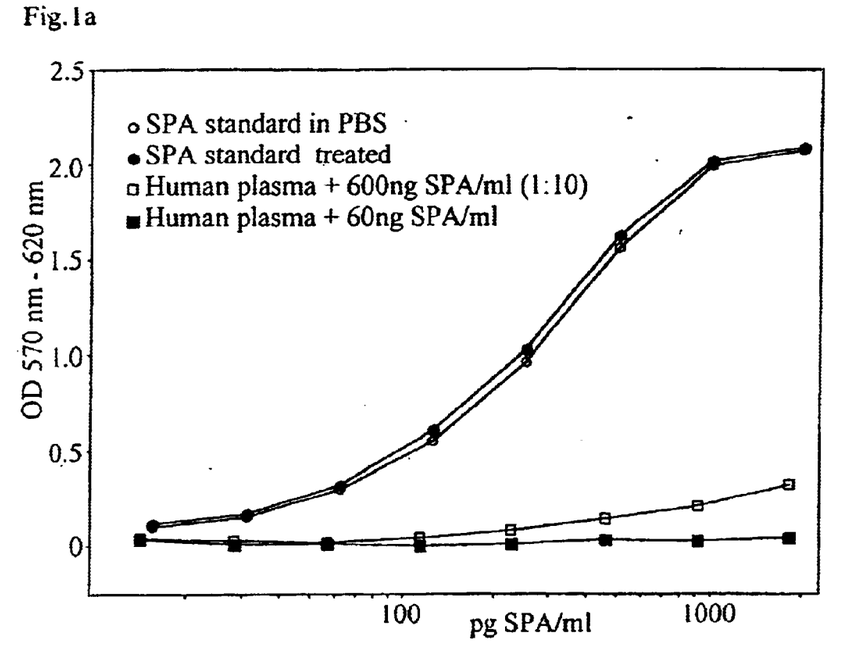
FIG. 1a–1d: A comparison of retrieval native *staphylococcus aureus* protein A (SPA) by means of ELISA added to human plasma in relation to the incubation period at 100° C. (in a water bath, 0, 30, 60, and 120 min). These samples were diluted according to the method of the present invention.
Figure 1B:
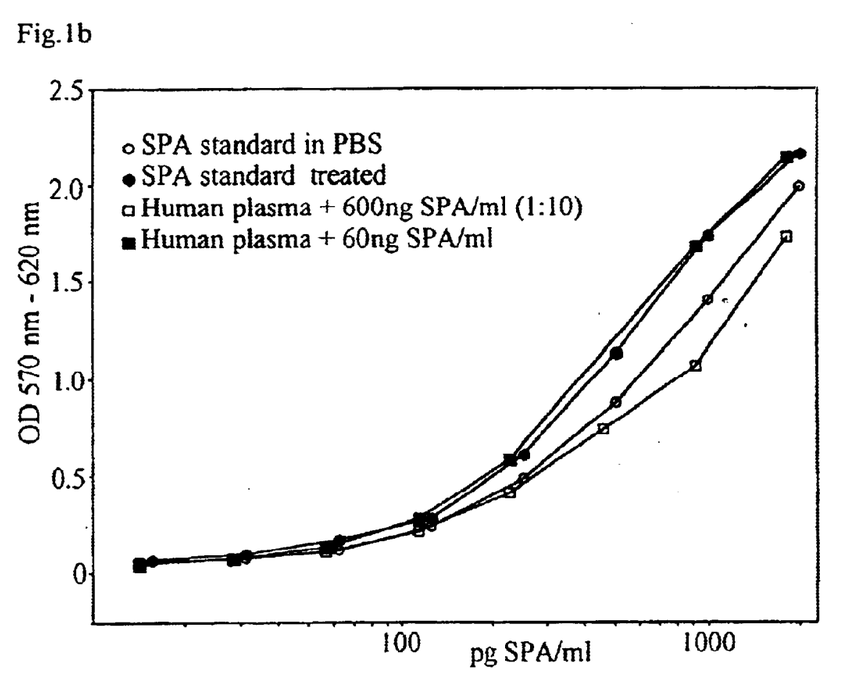
Figure 1C:
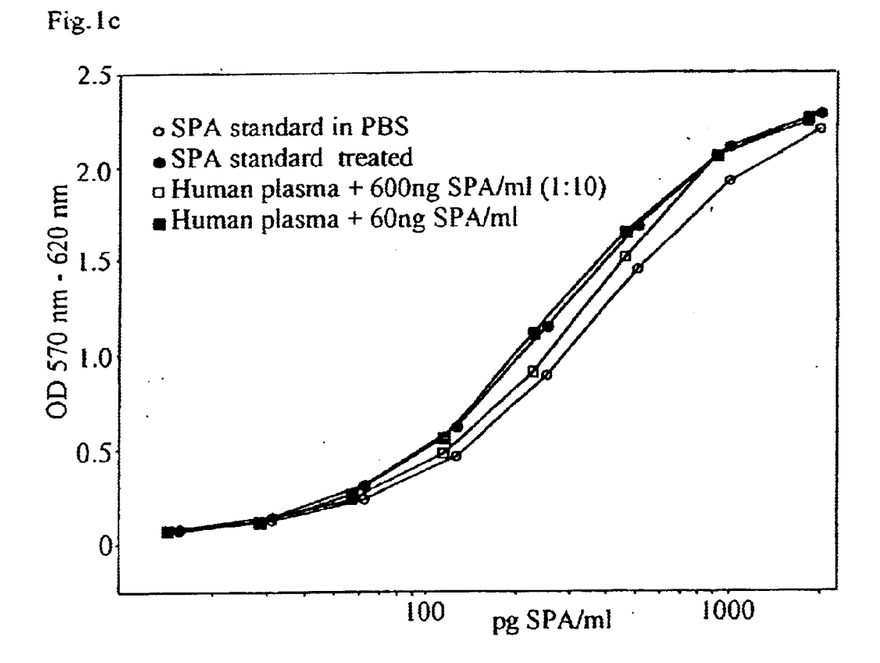
Figure 1D:
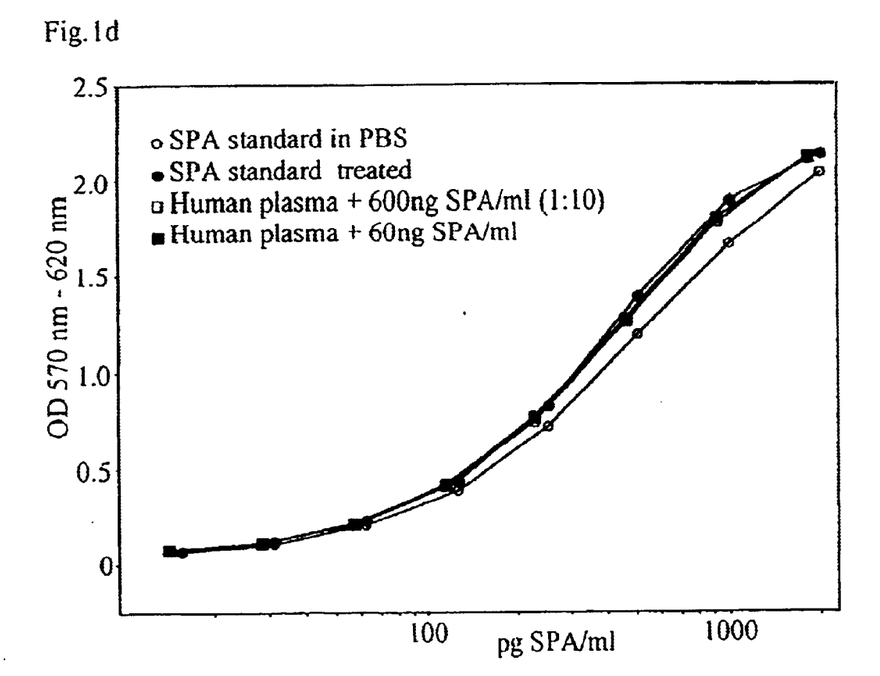
Figure 1E:
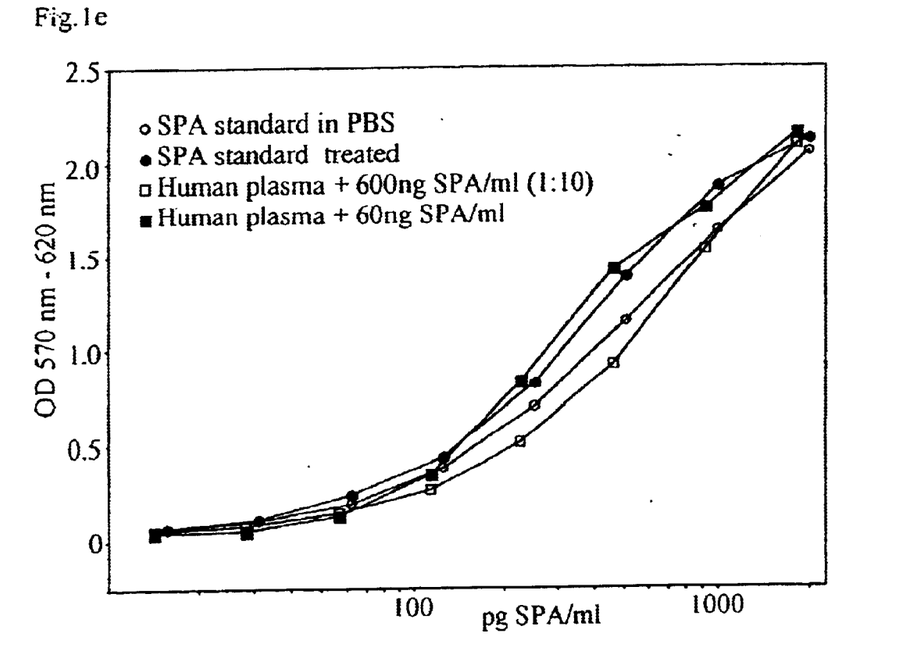
FIG. 1e: A comparison of the availability of SPA in the assay if the sample aliquots shown in FIG. 1d were diluted in dilution buffer in the assay without adding reagent.

FIG. 1e: A comparison of the availability of SPA in the assay if the sample aliquots shown in FIG. 1d were diluted in dilution buffer in the assay without adding reagent.

Figure 1F:
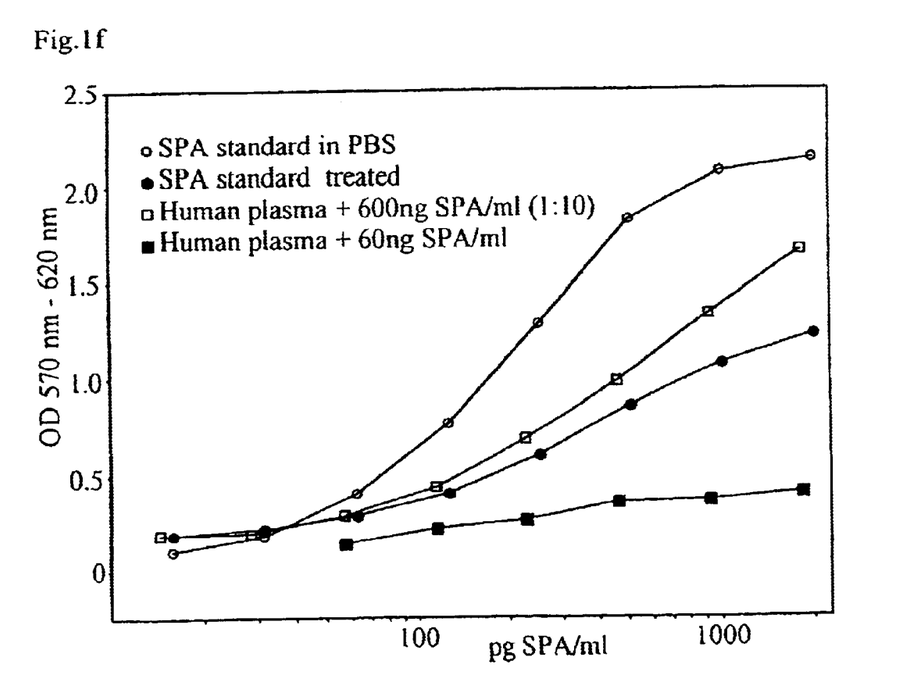
FIG. 1f: The results obtained according to the prior art method from these samples (acid dissociation).

FIG. 1f: The results obtained according to the prior art method from these samples (acid dissociation).

The following examples and comparative experiments are intended to further explain the present invention.

Example 1

The object of this example is the determination of reactivity of native staphylococcus aureus protein A (SPA) in a specific ELISA in the absence and in the presence of human IgG antibodies having high affinity, the determination of protein release at various incubation periods at 100° C. (cf. FIG. 1a–1d), the determination of the extent of renaturation of binding sites if no reagent is added to the sample dilution buffer at an appropriate concentration (FIG. 1e), and the comparison of the method according to the present invention with the method according to prior art (acid dissociation, FIG. 1f).

Figure 5:
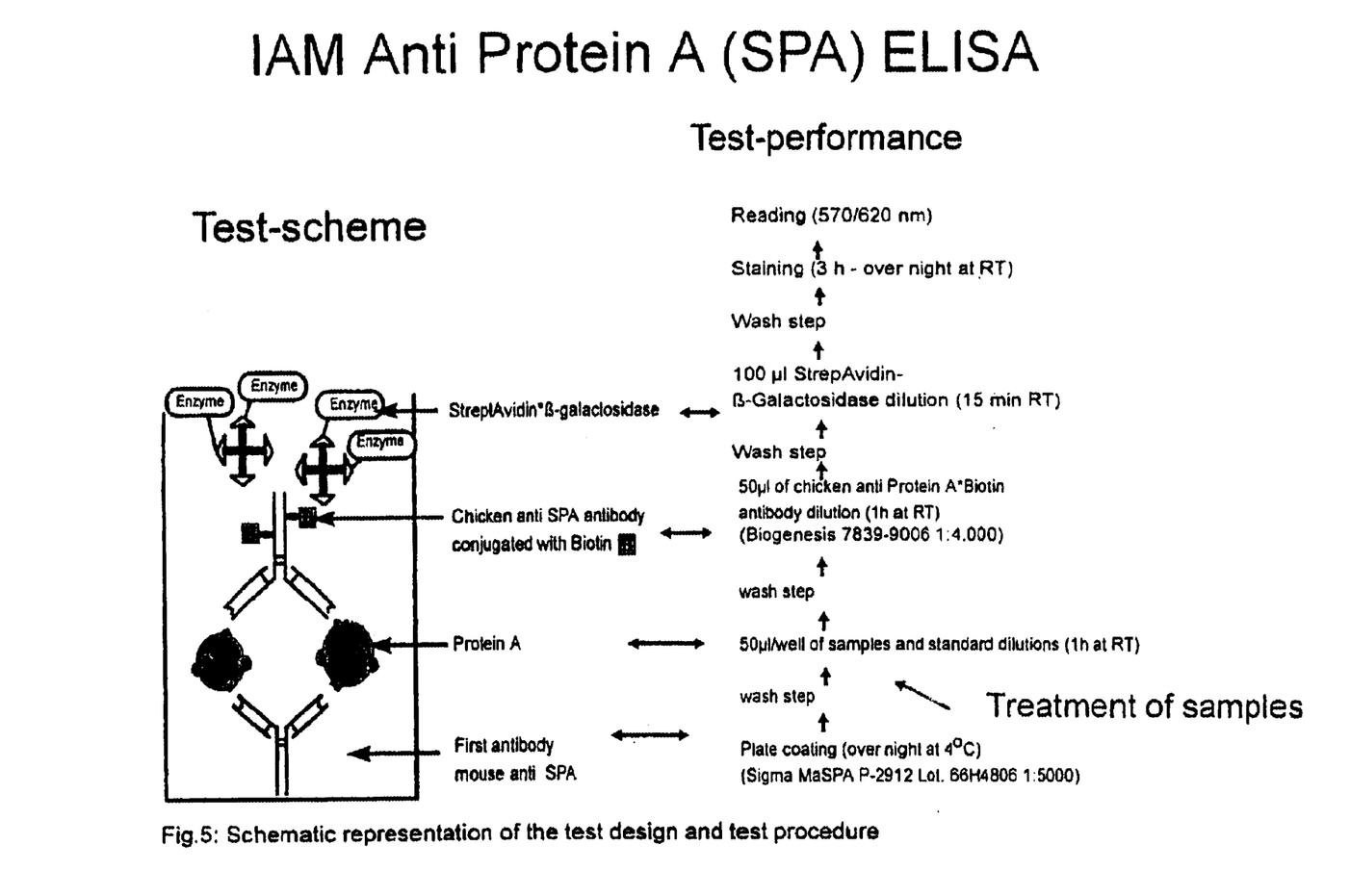
FIG. 5: Schematic representation of assay setup and implementation of anti-protein A double antibody sandwich ELISAs.

1.1. Materials and Method:

A sensitive anti protein A ELISA was established at the IAM (Institute of Applied Microbiology, Vienna). Assay scheme and implementation are shown in FIG. 5. A monoclonal mouse anti-SPA (P-2921, Sigma, St. Louis, U.S.A.) was used as a capture antibody. The second antibody in the assay (chicken anti-protein A, Biogenesis 7839-9006) was biotinylated with NHS-biotin (N-hydroxy succin imide activated biotin, Amersham Pharmacia Biotech, England). This ELISA is similarly suitable for both native and recombinant SPA from Amersham Pharmacia Biotech.

Eight 1:2 dilutions of the standard SPA protein were prepared as duplicates on each test plate (standard range 2000–15.6 pg SPA/ml). In these examples, highly pure native SPA (Amersham Pharmacia Biotech, Uppsala, Sweden, Lot no. T-249789) was used as SPA standard and to spike different sample matrixes with antibodies.

The various standards for protein A (native protein A lot T-249789, recombinant protein A lot T-238881) were obtained in lyophilized form. The standard proteins were weighed in, dissolved in distilled water, then the optical density at 275 nm was determined, and the protein A content was calculated by means of the appropriate molar extinction coefficient. The standard proteins were prediluted in PBS-TP, aliquoted and stored at −30° C.

SPA negative human plasma was obtained from Octapharma, Vienna.

EAR400 was used as ELISA Reader, and D-Soft from SLT (Grödig, Austria) was used as evaluation software. SDS was from Merck, Darmstadt, DTPA and polyvinylpyrrolidone (PVP-T40) from Sigma, St. Louis, U.S.A., bovine serum albumin from Hamosan (Ilz, Austria).

ELISA-Buffer:
 Coating buffer:
  0.1N $NaHCO_3$ buffer, pH=9.6–9.8
  8.4 g/l of $NaHCO_3$
  4.0 g/l of $Na_2CO_3$
  storage life: 1 week at 20° C.
 Washing buffer:
  PBS, pH=7.2–7.4
  1.15 g/l of $Na_2HPO_4.2H_2O$
  0.2 g/l of $KH_2PO_4$
  0.2 g/l of KCl
  8.0 g/l of NaCl
  1 ml of Tween20
  storage life: 1 day at 20° C.
 Sample preparation:
  Samples are diluted 1:5 in washing buffer+5% BSA, then diluted 1:3 in reagent solution (2% SDS 0.1% DTPA), mixed well and incubated at 100° C. for 120 min.
 Dilution buffer:
  Washing buffer+1% PVP+reagent solution 1:100 storage life: 1 day at 20° C.
 Conjugate buffer (SA*β-galactosidase):
  Dilution buffer+2 mM $MgCl_2$
 Staining buffer: pH=7.6
  10 mM imidazole
  2 mM $MgCl_2$
  1M NaCl
  adjust with 1 N HCl
 β-galactosidase substrate:
  Resorufin β-D-galactopyranside: 1 mg dissolved in 100 µl of DMSO was diluted in 10 ml of staining buffer.
  100 µl of staining solution/well applied 1.2. Implementation of the experiment:

SPA standard (3 mg/ml) was diluted in phosphate buffered saline solution (PBS) with 0.1% Tween20 (PBST) and with 1% polyvinylpyrrolidone (PBS-TP) in a parallel fashion and added to human plasma in 10 times concentrated form (10 plasma+1 SPA solution). The samples were mixed and incubated at room temperature for 1 h. [To each 2 ml of human plasma were added 200 µl of SPA solution (6 µg/ml or 600 ng/ml) in PBS+0.1% Tween20+1% PVP=545.4 ng of SPA/ml and 54.5 ng of SPA/ml, respectively.]

Subsequently, aliquots were treated according to the prior art method and according to the method of the present invention (as described below). The untreated samples were each diluted in the appropriate medium. A 1:2 dilution series was prepared from all treated and untreated samples and standards (8 dilution steps), and aliquots were transferred to the test plates.

Assay Nethod at Acid pH (Comparative Assay, State of the Art):

The samples and standards were prediluted in 0.5 M acetate/HCl buffer (pH=3,5) with 0.1 M NaCl and 0.1% Tween20, and the dilution series for the assays were similarly prepared in this buffer. Aliquots of the dilution series (50 µl) were transferred to 96 well test plates and incubated at room temperature for 60 min.

Method According to the Present Invention:

The samples were prediluted in 1:5 in PBS with 5% BSA (bovine serum albumin) or egg albumin (50 μl of sample+ 200 μl of BSA solution), then diluted 1:3 with reagent solution, mixed and incubated in screw-top reaction vessels in a water bath at 100° C. for 120 min. Aliquots of the dilution series (50 μl) in PBS-TP+7 mM SDS and 25 μM DTPA were transferred to 96 well test plates and incubated at room temperature for 60 min.

The concentration of the reagent solution used in this 1:5 predilution with 5% BSA solution was 70 mM SDS (=2%), 2.5 mM DTPA (=0.1%). This corresponds to a 100-fold molar excess of SDS over protein. In order to prevent renaturation of the antibody heavy chains, the reagent solution was added to the sangple dilution buffer at a ratio of 1:100 in the assay. Human plasma was spiked with native SPA (545 ng and 54.5 ng/ml, respectively) and diluted 1:5 in 5% BSA solution and then 1:3 in 70 mM SDS+2.5 mM DTPA solution. The samples containing 545 ng of SPA were subsequently diluted 1:20 in PBS-TP+reagent (1:100), samples containing 54,5 ng of SPA 1:2, and subsequently eightfold 1:2 in series. The standard protein A (60 ng/ml) was diluted and treated like the sample containing 54.5 ng of SPA/ml (=SPA standard treatment). SPA tends to dimerize in solution. This can lead to reduced detection in the assay. Therefore, SPA was applied diluted only in PBS+0.1% Tween20+1% PVP (standard in PBS) in order to demonstrate that monomerization will also take place under heat treatment for an appropriately long period and at appropriate SDS concentration.

This mixing ratio of "samples—protein solution— reaction solution" (1+4+10) is generally suitable for all common sample matrixes (in protein purification), for plasma and serum samples in order to obtain quantitative release and detection of bound SPA. Due to the high dilution ratio of sample:protein solution (1:5), possible reductions in dissociation, e.g. by too many SDS molecules adsorbing to buffer ions containing amino groups, are sufficiently buffered. If required for sensitivity, the dilution ratio may be reduced, observing the protein:SDS ratio (in the case of samples without buffer systems containing amino groups and having a pH of 5–8.5).

1.3. Ad FIG. 1a–1f

FIG. 1a shows the results of the anti SPA ELISA without heat treatment. It is obvious that in the human plasma sample, to which 60 ng SPA/ml has been added, no, and in the sample containing 600 ng of SPA/ml, only very little amounts are available in the assay.

FIG. 1b shows that after 30 min of heat treatment at 100° C., SPA in the sample containing 54.5 ng/ml is already quantitatively available, in the sample containing 545 ng of SPA/ml, however, only about 50% are available.

FIG. 1c shows that after 60 min of heat treatment, SPA is almost quantitatively available even in the sample containing 545 ng/ml.

FIG. 1d shows the quantitative release of SPA in both samples (54.5 ng and 545 ng of SPA/ml, respectively) after 120 min of heat treatment at 100° C.

FIGS. 1a to 1d clearly show how after 120 min the samples and standard curves become congruent, resulting in 100% retrieval. In order to show that the heavy chains of IgG antibodies may renaturate proportionately after this treatment in the region where protein A binds and may again react with SPA if the SDS concentration is too low, the samples shown in FIG. 1d were diluted in the assay dilution buffer without adding reagent in a parallel fashion and tested analoguously.

FIG. 1e shows how the slope of the sample dilution series and the retrieval changes as compared to the SPA standard treated in the same way if SDS is excessively diluted. This can be prevented by adding 0.7 mM SDS to the sample dilution buffer in the assay, as can be seen in FIG. 1e.

FIG. 1f shows how reactivity (slope) of the sample dilution series and retrieval in an acid environment (pH=3.5) change as compared to the standard in PBS (pH=7.3) and the SPA standard treated in a similar way. In this method, even very small differences in the pH of the samples will affect the results. The sample containing 545 ng of SPA/ml was prediluted 1:300, and the sample containing 54.5 ng of SPA/ml 1:30, in 0.5 M acetate buffer with 0.1 M NaCl and 0.1% Tween20.

Example 2

Determination of retrieval of SPA from complexes having formed in rabbit anti-SPA serum after addition of SPA and incubation (1 h at 37° C.). The presence of many specific antibodies allows even stronger and more intensive crosslinking and complex formation.

2.1. Materials and Method

Instead of human plasma, rabbit anti-SPA serum (Amersham Pharmacia Biotech, Uppsala, Sweden; serum no. 1183) was spiked with native SPA at 2 different concentrations (545 ng/ml and 54.5 ng/ml). Otherwise, this example was carried out as example 1.

2.2. Implementation of the Experiment

SPA standard (3 mg/ml) was diluted in phosphate buffered saline solution (PBS) with 0.1% Tween20 (PBST) and with 1% polyvinylpyrrolidone (PBS-TP) in a parallel fashion and added to rabbit anti SPA serum in 10 times concentrated form (10 serum+1 SPA solution). The samples were mixed and incubated at room temperature for 1 h.

Subsequently, aliquots were treated according to the prior art method and according to the method of the present invention (as described below). The untreated samples were each diluted in the appropriate medium. A 1:2 dilution series was prepared from all treated and untreated samples and standards (8 dilution steps), and aliquots were transferred to the test plates.

2.3. Ad FIG. 2a–2c

Figure 2A:
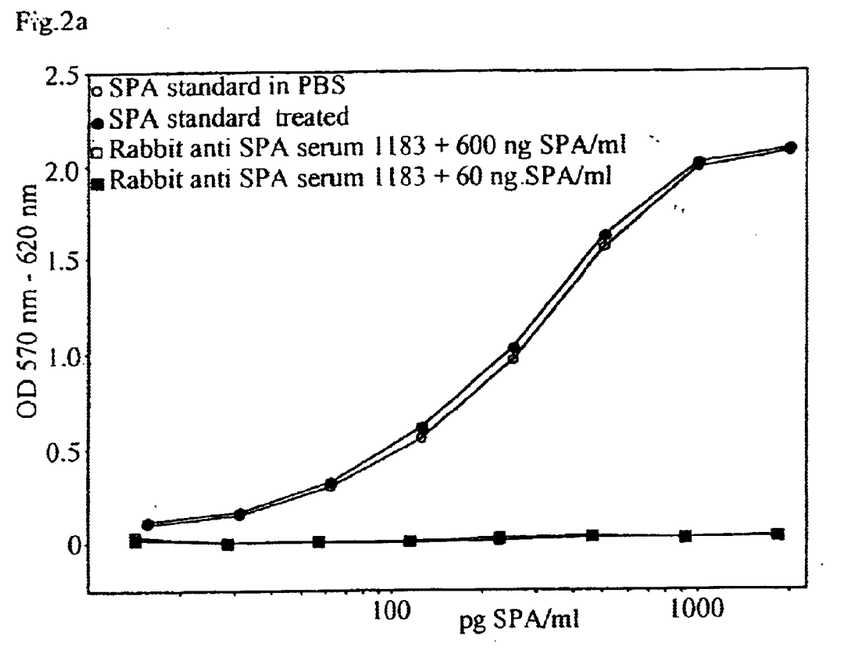
FIG. 2a–2c: A comparison of the method according to the present invention with the prior art method in the case of protein A retrieval from complexes having formed in rabbit anti-protein A serum.

FIG. 2a shows the results without heat treatment. It is obvious that no SPA is detectable even in the sample containing 545 ng of SPA/ml.

Figure 2B:
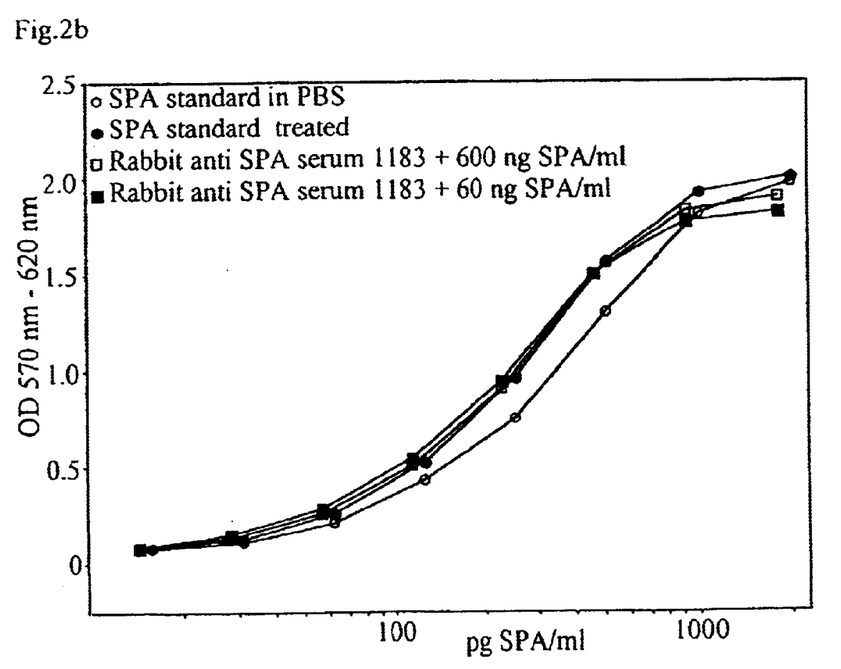

FIG. 2b shows that after 120 min of heat treatment at 100° C., similarly to the results from human plasma (FIG. 1d), SPA added to the two samples (545 ng and 54.5 ng of SPA/ml, respectively) is quantitatively released and detectable.

Figure 2C:
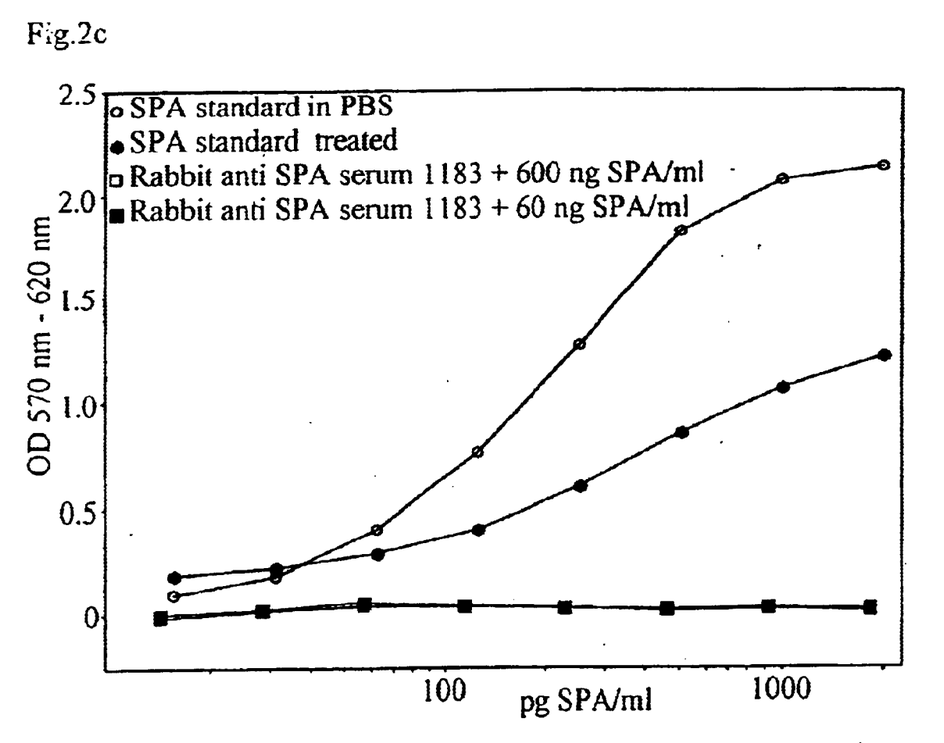

FIG. 2c shows that in this case, no SPA is released and detectable according to the prior art method. The 545 ng of SPA/ml sample was prediluted 1:300, the 54.5 ng of SPA/ml sample 1:30, in 0.5M acetate buffer with 0.1M NaCl and 0.1% Tween 20.

Example 3

Determination of retrieval of recombinant SPA from complexes having formed with polyclonal human IgG (1 mg of IgG/ml) after addition of SPA and incubation (1 h at 37° C.).

Native as well as differently modified recombinant SPA are used as immunoligands for IgG purification. Therefore, it is important that the method according to the invention for dissociation and the assay system are equally suitable for the various modifications.

3.1. Materials and Method

Polyclonal human IgG, pre-purified by means of Cohn precipitation and gel filtration, was spiked with recombinant SPA (Amersham Pharmacia Biotech, Uppsala, Sweden, lot no. 238881) at 2 different concentrations (545 ng/ml and 54.5 ng/ml). Otherwise this example was carried out according to example 1.

3.2. Implementation of the Experiment

Polyclonal IgG (Cohn fraction, Immuno, Vienna) was concentrated dissolved in PBS (30 mg/ml) and gel filtrated. The concentration was determined by means of anti-human IgG ELISA. Recombinant SPA standard (3 mg/ml) in phosphate buffered saline solution (PBS) was diluted with 0.1% Tween20 (PBST) and with 1% polyvinylpyrrolidone (PBS-TP) in a parallel fashion, and added, in 10 times concentrated form (6 µg/ml and 600 ng/ml, respectively), to the IgG solution at 1.1 mg/ml (10 parts of IgG solution+1 part of SPA solution). The samples were mixed and incubated at room temperature for 1 h.

Then aliquots were treated according to the prior art method and according to the method of the present invention (as described below). The untreated samples were diluted in the corresponding medium. A 1:2 dilution series (8 dilution steps) was prepared from all treated and untreated samples and standards, and aliquots were transferred to the test plates.

3.3. Ad FIG. 3a–3c

Figure 3A:
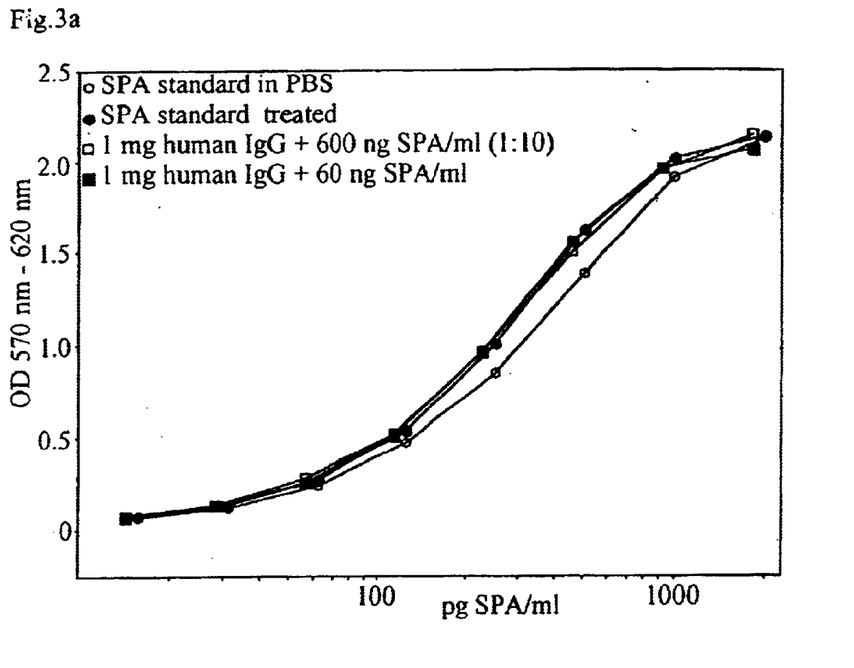
FIG. 3a–3b: A comparison of the method according to the present invention with the prior art method in the case of protein A retrieval from complexes having formed in the presence of 1 mg of human polyclonal IgG/ml.

FIG. 3a shows that after 120 min of heat treatment at 100° C. the added recombinant SPA in both samples (545 ng and 54.5 ng of SPA/ml) is quantitatively released and detectable even in samples containing prepurified polyclonal human IgG at an antibody concentration of 1 mg of IgG/ml.

Figure 3B:
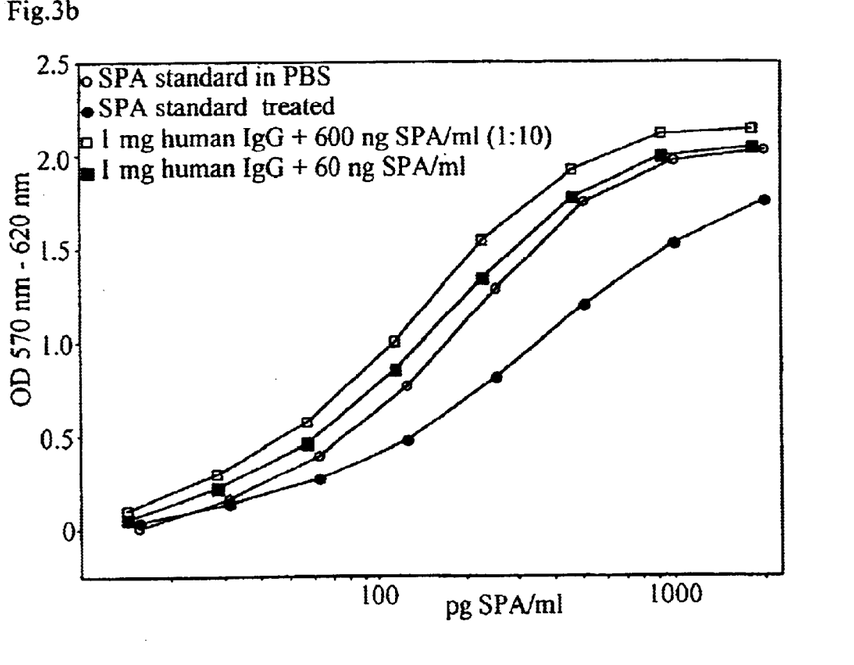

FIG. 3b shows that reactivity at a pH of 3.5 is highly dependent on the total ionic strength and on slight changes in pH in the samples, and that, above all, undissolved complexes can even give the illusion of an excessively high SPA content as compared to the standard. The sample containing 545 ng of SPA/ml was prediluted 1:300, and the sample containing 54.5 ng of SPA/ml 1:30, in 0.5M acetate buffer with 0.1M NaCl and 0.1% Tween20.

Example 4

Determination of retrieval of recombinant SPA from complexes having formed at high polyclonal human IgG (10 mg of IgG/ml) content after addition of SPA and incubation (1 h at 37° C.).

4.1. Materials and Method

Polyclonal human IgG, prepurified by means of Cohn precipitation and gel filtration, was spiked with recombinant SPA (Amersham Pharmacia Biotech, Uppsala, Sweden. lot no. 238881) at 2 different concentrations (545 ng/ml and 54.5 ng/ml). Otherwise, this example was carried out according to example 1.

4.2. Implementation of the Experiment

Polyclonal IgG (Cohn fraction, Immuno, Vienna) was concentrated dissolved in PBS (30 mg/ml) and gel filtrated. The concentration was determined by means of anti human IgG ELISA. Recombinant SPA standard (3 mg/ml) was diluted in a parallel fashion in phosphate buffered saline solution (PBS) with 0.1% Tween 20 (PBST) and with 1% polyvinylpyrrolidone (PBS-TP), and added, in 10 times concentrated form (6 µg/ml and 600 ng/ml, respectively), to the IgG solution at 11 mg/ml (10 parts of IgG solution+1 part of SPA solution). The samples were mixed and incubated at room temperature for 1 h.

Then aliquots were treated according to the prior art method and according to the method of the present invention (as described below): The untreated samples were each diluted in the appropriate medium. A 1:2 dilution series (8 dilution steps) was prepared from all treated and untreated samples and standards, and aliquots were transferred to the test plates.

4.3. Ad FIG. 4a–4c

Figure 4A:
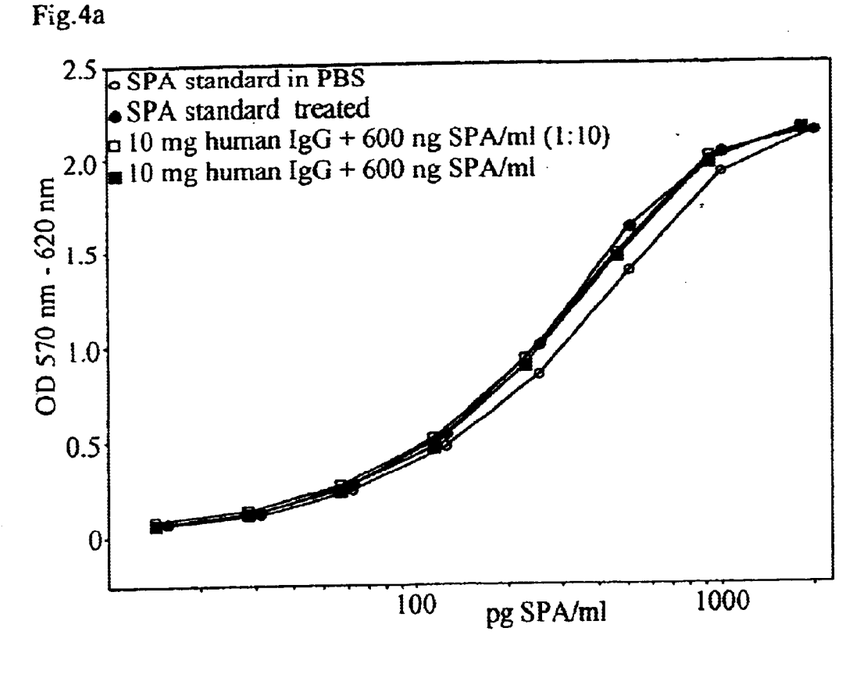
FIG. 4a–4b: A comparison of the method according to the present invention with the prior art method in the case of protein A retrieval from complexes having formed in the presence of 10 mg of human polyclonal IgG/mi.

FIG. 4a shows that after 120 min of heat treatment at 100° C. the added recombinant SPA in both samples (545 ng and 54.5 ng of SPA/ml) is quantitatively released and detectable even in samples containing prepurified polyclonal human IgG at an antibody concentration of 10 mg of IgG/ml.

Figure 4B:
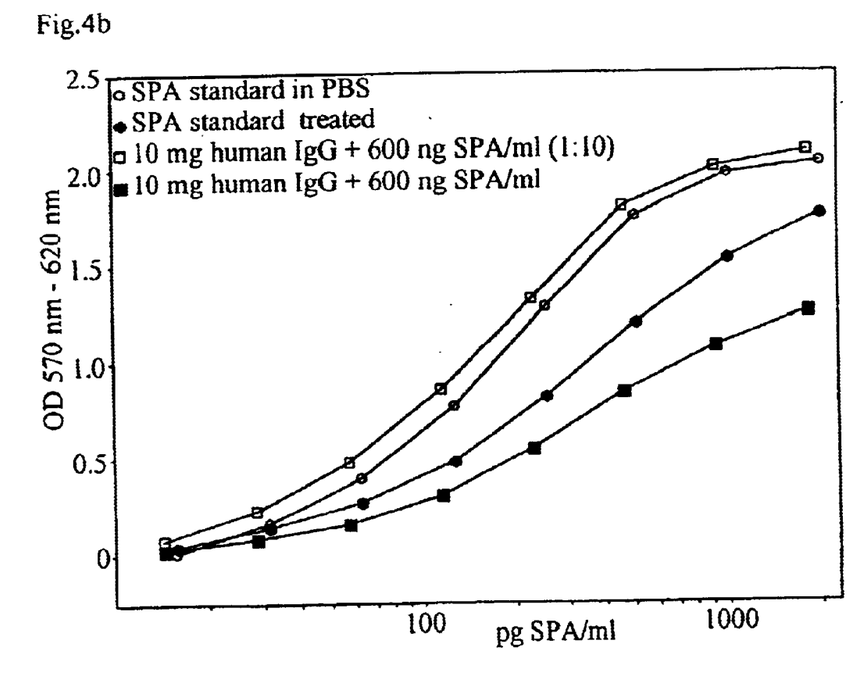

FIG. 4b shows that reactivity of SPA with IgG is dependent on the concentration ratio (cf. FIG. 3a). As opposed to the method according to the present invention, the SPA content in these samples can not be determined correctly by the prior art method (cf. FIGS. 1–3). The sample containing 545 ng of SPA/ml was prediluted 1:300, and the sample containing 54.5 ng of SPA/ml 1:30, in 0.5M acetate buffer with 0.1M NaCl and 0.1% of Tween 20.

What is claimed is:

1. A method of releasing thermostable immunoligands bound to the Fc-part of immunoglobulins in immunoglobulin-immunoligand complexes and preventing rebinding thereof, and assaying said thermostable immunoligands comprising:

prediluting a sample containing said immunoglobulin-immunoligand complexes, with a buffered solution having a defined protein content;

mixing said prediluted sample with a reagent compound that binds non-specifically or adsorbs to said immunoglobulins;

heating said prediluted sample mixed with reagent compound thereby releasing said thermostable immunoligands from said Fc-part;

thereafter, cooling said prediluted sample mixed with reagent compound; and carrying out an immunochemical assay on said prediluted sample mixed with reagent compound to detect, or detect and quantify said thermostable immunoligands, wherein said prediluted sample mixed with reagent compound is further combined with sample dilution buffer used in the assay, said sample dilution buffer having a solution of said reagent compound added thereto, in a concentration that prevents rebinding of said thermostable immunoligands to said Fc-part.

2. The method according to claim 1, wherein a chelator is added before the heating step in order to bind heavy metal ions.

3. The method according to claim 1, wherein said reagent compound has a hydrophobic as well as negatively charged ends.

4. The method according to claim 1, wherein said reagent compound is sodium dodecyl sulfate (SDS).

5. The method according to claim 1, wherein said reagent compound in the sample before heating has a concentration within a range of 10 to 40 mM.

6. The method according to claim 5, wherein said concentration is within a range of 30 to 40 mM.

7. The method according to claim 1, wherein said heating step is applied during a time period within a range of 3 to 180 minutes and at a temperature within a range of 60 to 100° C.

8. The method according to claim 1, wherein during said cooling step, said sample with reagent compound is allowed to go down to a temperature within a range of 0 to 40° C.

9. The method according to claim 8, wherein said sample with reagent compound is allowed to go down to a temperature within a range of 4 to 35° C.

10. The method according to claim 1, wherein said sample with reagent during said heating has a pH within a range of 5 to 8.

11. The method according to claim 10, wherein said sample with reagent during said heating has a pH within a range of 6 to 7.5.

12. The method according to claim 1, wherein said buffered solution is a borate buffered solution.

13. The method according to claim 1, wherein said buffered solution has a concentration within a range of 5 to 100 mM.

14. The method according to claim 1, wherein said protein in the sample before the heating step has a concentration within a range of 1/20 to 1/100 of the concentration of said reagent compound.

15. The method of claim 14, wherein said protein in the sample before the heating step has a concentration within a range of 0.3 to 2 mM.

16. The method of claim 2, wherein said chelator is present in the sample before the heating step, in a concentration within a range of 0.5 to 5 mM.

17. The method of claim 1, wherein said buffered solution is a phosphate buffered solution.

18. The method according to claim 1, wherein said solution of said reagent compound comprises sodium dodecylhydrogensulfate (SDS) and a chelating agent.

19. The method of claim 18, wherein said chelating agent is diethyleiie triamine pentaacetic acid (DETAPAC) or ethylene diamine tetraacetic acid (EDTA).

20. The method according to claim 17, wherein said sample is of unknown compostion and said sample is prediluted with said phosphate buffered solution having a defined protein content at a ratio of 1:4, and this mixture is then mixed with said solution of said reagent compound at a ratio of 1:2.

21. The method according to claim 18, wherein said solution of said reagent compound is added to the sample dilution buffer used in the assay up to a concentration of 0.02% free SDS in the sample dilution buffer.

22. The method according to claim 1, wherein said heating of the prediluted sample to be assayed, takes place at 100° C. for 2 hours, followed by cooling to room temperature.

23. The method according to claim 17, wherein the phosphate buffered solution having a defined protein content, and the solution of said reagent compound, is adjusted to a pH of 6.0–7.5 by means of 1N NaOH or 1N HCl.

24. The method according to claim 1, wherein the mixing of sample, to buffered solution having a defined protein content, to the solution of said reagent compound is at a ratio of 1:4:10, respectively.

25. The method according to claim 17, wherein said phosphate buffered solution having a defined protein content comprises $Na_2HPO_4 \cdot 2H_2O$, $KH_2PO_4$, KCl, NaCl and protein selected from the group consisting of bovine serum albumin, egg albumin, albumin and mixtures thereof.

* * * * *